(12) United States Patent
Ralph (10) Patent No.: US 6,984,494 B2
(45) Date of Patent: Jan. 10, 2006

(54) ANALYTICAL METHOD

(75) Inventor: Peter Ralph, Orinda, CA (US)

(73) Assignee: Genentech, Inc., South San Francisco, CA (US)

( * ) Notice: Subject to any disclaimer, the term of this patent is extended or adjusted under 35 U.S.C. 154(b) by 696 days.

(21) Appl. No.: 09/921,161

(22) Filed: Aug. 1, 2001

(65) Prior Publication Data

US 2002/0090662 A1 Jul. 11, 2002

Related U.S. Application Data (60) Provisional application No. 60/225,433, filed on Aug. 15, 2000.

(51) Int. Cl.
  *G01N 33/53* (2006.01)

(52) U.S. Cl. .................. 435/7.1; 435/7.9; 435/7.91; 435/962; 435/973

(58) Field of Classification Search ................ 435/962, 435/973, 7.1, 7.9, 7.91
See application file for complete search history.

(56) References Cited

U.S. PATENT DOCUMENTS

| | | | | |
|---|---|---|---|---|
| 4,803,154 A | * | 2/1989 | Uo et al. | .................... 435/7.93 |
| 4,968,603 A | | 11/1990 | Slamon et al. | |
| 5,480,792 A | | 1/1996 | Buechler et al. | |
| 5,501,983 A | | 3/1996 | Lilja et al. | |
| 5,518,887 A | * | 5/1996 | Parsons et al. | ............... 435/7.1 |
| 5,821,337 A | | 10/1998 | Carter et al. | |

OTHER PUBLICATIONS

Aasland et al., "Expression of oncogenes in thyroid tumours: Coexpression of c–erb B2/neu and c–erbB" *Br. J. Cancer* 57:358–363 (1988).
Baselga et al., "Phase II Study of Weekly Intravenous Recombinant Humanized Anti–p185 $^{HER2}$ Monoclonal Antibody in Patients with HER2/neu–Overexpressiing Metastatic Breast Cancer" *J. Clin. Oncol.* 14:737–744 (1996).
Bastiaens and Squire, "Fluorescene lifetime imaging microscopy: spatial resolution of biochemical processes in the cell" *Trends Cells Biol.* 9:48–52 (1999).
Borst et al., "Oncogene Alterations in Endometrial Carcinoma" *Gynecol. Oncol.*, 38:364 (1990).
Carter et al., "Humanization of an anti–p185 HER2 antibody for human cancer therapy" *Proc. Natl. Acad. Sci. USA* 89: 4285 (1992).
Cohen et al., "Expression pattern of the neu (NGL) gene–encoded growth factor receptor protein (p185 $^{neu}$) in normal and transformed tissues of the disgestive tract" *Oncogene*, 4:81–88 (1989).
Fehm et al., "The Prognostic Significance of c–erbB–2 Serum Protein in Metastatic Breast Cancer" *Oncology* 55:33–38 (1998).
Fukushigi et al., "Localization of a Novel v–erbB–Related Gene, c–erbB–2, on Human Chromosome 17 and Its Amplification in a Gastric Cancer Cell Line" *Mol Cell Biol.*, 6:955–958 (1986).
Geurin et al., "Overexpression of Either c–myc or c–erbB–2/neu Proto–Oncogenes in Human Breast Carcinomas: Correlation with Poor Prognosis" *Oncogene Res.*, 3:21–31 (1988).
Gu et al., "Overexpression of her–2/neu in human prostate cancer and benign hyoerplasia" *Cancer Lett.* 99:185–9 (1996).
Hudziak et al., "p185$^{HER2}$ Monoclonal Antibody Has Antiproliferative Effects In Vitro and Sensitizes Human Breast Tumor Cells to Tumor Necrosis Factor" *Mol. Cell. Biol.* 9(3):1165–1172 (1989).
Kern et al., "p185$^{neu}$ Expression in Human Lung Adenocarcinomas Predicts Shortened Survival" *Cancer Res.*, 50:5184 (1990).
King et al., "Amplification of a Novel v–erbB–Related Gene in a Human Mammary Carcinome" *Science*, 229:974 (1985).
Kobayashi et al. "Detectuib of Microfilarial Antigen in Circulating Immune Complex from Sera of Wuchereria Bancrofti–infected individuals" *Am. J. Trop. Med. Hyg.* 57: 200–204 (1997).
Park et al., "Amplification, Overexpression, and Rearrangement of the erbB–2 Protooncogene in Primary Human Stomach Carcinomas" *Cancer Res.*, 49:6605 (1989).
Ross et al. "Prognostic Significance of HER–2/neu Gene" *Cancer* 79:2162–70 (1997).
Ross et al., "HER–2/neu Gene Amplification Status in Prostate Cancer by Fluorescence in Situ Hybridization" *Hum. Pathol.* 28:827–33 (1997).
Sadasivan et al., "Overexpression of HER–2/neu May be an Indicator of Poor Prognosis in Prostate Cancer" *J. Urol.* 150:126–31 (1993).
Schmerr et al., "Improvements in a competition assay to detect scrapie prion protein by capillary electrophoresis" *J. Chromatogr. B. Biomed. Appl.* 681: 29–35 (1996).
Sch˙upbach et al., "Heat–mediated immune complex dissociation and enzyme–linked immunosorbent assay signal amplification render p24 antigen detection in plasma as sensitive as HIV–1 RNA detection by polymerase chain reaction" *J. Infect. Dis.* 170: 318–324 (1994).
Slamon et al., "Human Breast Cancer: Correlation of Relapse and Survival with Amplification of the HER–2/neu Oncogene" *Science*, 235:177–182 (1987).
Slamon et al., "Studies of the HER–2/neu Proto–oncogene in Human Breast and Ovarian Cancer" *Science*, 244:707–712 (1989).

(Continued)

*Primary Examiner*—Long V. Le
*Assistant Examiner*—Jacob Cheu
(74) *Attorney, Agent, or Firm*—Wendy Lee; Ginger R. Dreger, Esq.; Heller Ehrman LLP (57) ABSTRACT

The instant invention describes an analytical assay to accurately measure an analyte in the presence of an interfering substance.

22 Claims, 3 Drawing Sheets

OTHER PUBLICATIONS

Steindl et al., "A simple and robust method for the complete dissociation of HIV–1 p24 and other antigens from immune complexes in serum and plasma samples" *J. Immunol. Methods* 217: 143–151 (1998).

Weiner et al., "Expression of the neu Gene–encoded Protein (P185$^{neu}$) in Human Non–Small Cell Carcinomas of the Lung" *Cancer Res.*, 50:421–425 (1990).

Williams et al., "Expression of c–erbB–2 in Human Pancreatic Adenicarcinomas" *Pathobiology* 59:46–52 (1991).

Yamauchi et al., "Prediction of Response to Antiestrogen Therapy in Advanced Breast Cancer Patients by Pretreatment Circulating Levels of Extracellular Dpomain of the HER–2/c–neu Protein" *J. Clin. Oncol.* 15: 2518–2525 (1997).

Yokota et al., "Amplification of c–erbB–2 Oncogene in Human Adenocarcinomas in Vivo" *Lancet:* 1:765–767 (1986).

Yonemura et al., "Evaluation of Immunoreactivity for erbB–2 Portein as a Marker of Poor Short Term Prognosis in Gastric Cancer" *Cancer Res.*, 51:1034 (1991).

Zhau et al., "Amplification and Expression of the c–erb B–2/neu Proto–Oncogene in Human Bladder Cancer" *Mol. Carcinog.*, 3:354–357 (1990).

* cited by examiner

| | | | | | |
|---|---|---|---|---|---|
| MELAALCRWG | LLLALLPPGA | ASTQVCTGTD | MKLRLPASPE | THLDMLRHLY | QGCQVVQGNL 60 |
| ELTYLPTNAS | LSFLQDIQEV | QGYVLIAHNQ | VRQVPLQRLR | IVRGTQLFED | NYALSVLDNG 120 |
| DPLNNTTPVT | GASPGGLREL | QLRSLTEILK | GGVLIQRNPQ | LCYQDTILWK | DIFHKNNQLA 180 |
| LTLIDTNRSR | ACHPCSPMCK | GSRCWGESSE | DCQSLTRTVC | AGGCARCKGP | LPTDCCHEQC 240 |
| AAGCTGPKHS | DCLACLHFNH | SGICELHCPA | LVTYNTDTFE | SMPNPEGRYT | FGASCVTACP 300 |
| YNYLSTDVGS | CTLVCPLHNQ | EVTAEDGTQR | CEKCSKPCAR | VCYGLGMEHL | REVRAVTSAN 360 |
| IQEFAGCKKI | FGSLAFLPES | FDGDPASNTA | PLQPEQLQVF | ETLEEITGYL | YISAWPDSLP 420 |
| DLSVFQNLQV | IRGRILHNGA | YSLTLQGLGI | SWLGLRSLRE | LGSGLALIHH | NTHLCFVHTV 480 |
| PWDQLFRNPH | QALLHTANRP | EDECVGEGLA | CHQLCARGHC | WGPGPTQCVN | CSQFLRGQEC 540 |
| VEECRVLQGL | PREYVNARHC | LPCHPECQPQ | NGSVTCFGPE | ADQCVACAHY | KDPPFCVARC 600 |
| PSGZKPDLSY | MPIWKFPDEE | GACQPCPINC | THSCVDLDDK | GCPAE | 645 |

SEQUENCE LISTING

<160> NUMBER OF SEQ ID NOS: 1

<210> SEQ ID NO 1
<211> LENGTH: 645
<212> TYPE: PRT
<213> ORGANISM: Homo sapiens

<400> SEQUENCE: 1

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255
```

-continued

```
His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
                290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
                370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
                450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640

Gly Cys Pro Ala Glu
                645
```

ANALYTICAL METHOD

This application claims the benefit under Title 35, United States Codes § 119(e) of the U.S. provisional Application No.: 60/225,433 filed on Aug. 15, 2000.

BACKGROUND OF THE INVENTION

1. Field of the Invention

The present invention concerns an analytical method developed to accurately quantitate an analyte in the presence of an interfering substance.

2. Description of the Related Art

Antibodies have been widely used to detect and estimate specific antigens amidst the mixture of complex molecules in samples. The specificity of interaction with antigens has made them a valuable tool in such immunoassays. The assays enable the detection and quantitation of a wide variety of molecules such as hormones, tumor antigens, bacterial or viral antigens, etc. in biological samples. The range of such immunoassays has considerably broadened as a result of advances made in elicitation and characterization of antibodies against a variety of molecules such as proteins, peptides, carbohydrates, lipids, nucleic acids and small molecular weight compounds. The advent of monoclonal antibodies has added a new dimension by greatly enhancing the specificity of the immunoassays. The utility of the methods has further widened as a result of the flexible format (liquid vs. solid-phase) and various methods of enhancing the sensitivity of the detection. Amplification of the signal has been achieved using enzymes, radioisotopes and chemiluminiscence. Radioimmunoassay (RIA), Enzyme Linked Immunosorbent Assay (ELISA), immunohistochemistry and Western blot are just a few examples of the versatile nature and general applicability of immunoassays.

Immunoassays are used today not only in the diagnosis of infection by specific pathogens, but also for screening blood supply to ensure that they are free of blood-borne viruses such as human immunodeficiency virus (HIV), hepatitis B virus (HBV), hepatitis C virus (HCV) etc. These assays are also widely used for the detection and/or pregnancy detection test, thyroid stimulating hormone (TSH), T3 and T4 for thyroid function test, human growth hormone (hGH) for various growth abnormalities, insulin for diabetes etc. Furthermore, immunoassays are also used to determine predisposition to certain conditions such as cancer. For example, serum level of prostate cancer antigen (PSA) is used to determine the onset of prostate cancer. Similarly, immunoassays also have great prognostic values. For instance, monitoring the level of HER2 expression in breast cancer patients is useful in predicting the success of a therapy based on the administration of HERCEPTIN® (Genentech, Inc., South San Francisco, Calif.), a recombinant humanized monoclonal antibody directed against p185$^{HER2/neu}$, since this therapy primarily targets patients showing overexpression of this oncoprotein.

One of the problems frequently encountered in the use of immunoassay in estimating the amount of an analyte present in a sample is the presence of interfering substances that bind to the analyte, which makes a fraction of the analyte unavailable for reaction with antibodies against the analyte. The consequence of this interference is underestimation of the amount of analyte. There are several methods designed to address this problem. For example, one could separate the analyte and interfering substance present in the sample, for instance by chromatography, prior to subjecting the sample to immunoassay. For detection of microfilarial antigen in circulating immune complex from sera of filaria-infected individuals, Kobayashi et al. (*Am. J. Trop. Med. Hyg.* 57: 200–204 [1997]) used acidification of the test sera to pH 2 followed by restoring to pH 6 and then applying to an ELISA plate. The inhibiting moiety thus denatured by acid exposure may no longer be able to bind ligand, or may reform complexes slowly as compared to the capture of the ligand by the coated antibodies. Immune complex formation causes underdetection of p24 antigen in human immunodeficiency virus (HIV) infection. This problem was reportedly overcome by briefly boiling diluted plasma samples that released all complexed antigen, which was then measured by conventional method (Schüpbach et al., *J. Infect. Dis.* 170: 318–324 [1994]). Steindl et al. (*J. Immunol. Methods* 217: 143–151 [1998]) approached the same problem with slightly different solution; they used heat denaturation combined with exposure to sodium dodecyl sulfate (SDS) and diethylenetriaminepentaacetic acid (DTPA) to successfully dissociate immune complexes. Similarly, exposure to a reducing agent (β-mercaptoethanol) and separation by free zone capillary electrophoresis was used to dissociate the aggregates of prion protein in order to estimate the level of free monomeric prions in bovine brain extract (Schmerr et al., *J. Chromatogr. B. Biomed. Appl.* 681: 29–35 [1996]). Another approach used to obviate this problem is described in a U.S. Pat. No. 5,501,983. In this instance, total prostate specific antigen (PSA) was estimated by separately measuring free PSA and PSA bound to proteinase inhibitor using two different assays. However, these approaches necessitate additional steps which are time consuming, cumbersome and often result in considerable loss of samples.

The present invention discloses a general strategy of accurately quantitating the amount of an analyte present in a fluid sample in the presence of an interfering substance. The strategy is exemplified by the application of this strategy for quantitative determination of serum HERCEPTIN® level in patients undergoing HERCEPTIN® therapy.

The ErbB family of receptor tyrosine kinases are important mediators of cell growth, differentiation and survival. The receptor family includes four distinct members including epidermal growth factor receptor (EGFR or ErbB1), HER2 (ErbB2 or p185$^{neu}$), HER3 (ErbB3) and HER4 (ErbB4). The second member of the ErbB family, p185$^{neu}$, was originally identified as the product of the transforming gene from neuroblastomas of chemically treated rats. Amplification of the human homolog of neu (i.e. HER2) is observed in breast and ovarian cancers and correlates with a poor prognosis (Slamon et al., *Science,* 235:177–182 (1987); Slamon et al., *Science,* 244:707–712 (1989); and U.S. Pat. No. 4,968,603). Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765–767 (1986); Fukushigi et al., *Mol Cell Biol.,* 6:955–958 (1986); Geurin et al., *Oncogene Res.,* 3:21–31 (1988); Cohen et al., *Oncogene,* 4:81–88 (1989); Yonemura et al, *Cancer Res.,* 51:1034 (1991); Borst et al., *Gynecol. Oncol.,* 38:364 (1990); Weiner et al., *Cancer Res.,* 50:421–425 (1990); Kern et al., *Cancer Res.,* 50:5184 (1990); Park et al., *Cancer Res.,* 49:6605 (1989); Zhau et al., *Mol. Carcinog.,* 3:354–357 (1990); Aasland et al. *Br. J. Cancer* 57:358–363 (1988); Williams et al. *Pathiobiology* 59:46–52 (1991); and McCann et al., *Cancer,* 65:88–92 (1990). ErbB2 may be overexpressed in prostate cancer (Gu et al. *Cancer Lett.* 99:185–9 (1996); Ross et al. *Hum. Pathol.* 28:827–33 (1997); Ross et al. *Cancer* 79:2162–70 (1997); and Sadasivan et al. *J. Urol.* 150:126–31 (1993)).

Hudziak et al., *Mol. Cell. Biol.* 9(3):1165–1172 (1989) describe the generation of a panel of anti-ErbB2 antibodies one of which, called 4D5, inhibited cellular proliferation by 56%. A recombinant humanized version of the murine anti-ErbB2 antibody 4D5 (huMAb4D5-8, rhuMAb HER2 or HERCEPTIN®; U.S. Pat. No. 5,821,337) is clinically active in patients with ErbB2-overexpressing metastatic breast cancers that have received extensive prior anti-cancer therapy (Baselga et al, *J. Clin. Oncol.* 14:737–744 (1996)). HERCEPTIN® received marketing approval from the Food and Drug Administration Sep. 25, 1998 for the treatment of patients with metastatic breast cancer whose tumors overexpress the ErbB2/HER2 protein. Since HER2 is also overexpressed in other cancers, in addition to breast cancer, HERCEPTIN® holds a great potential in the treatment of such other cancers as well.

As described above, HERCEPTIN® has been successfully used in the treatment of breast cancer. However, the level of serum HERCEPTIN® should be maintained at 5–10 µg/ml during the therapy in order to effectively inhibit the growth of HER2 overexpressing breast cancer cells. Monitoring the level of serum HERCEPTIN® is thus crucial in the course of HERCEPTIN® therapy. A specific ELISA for the detection and quantitation of HERCEPTIN®, using HER2 extracellular domain (ECD) as a capture reagent, has been developed (Baselga et al., *J. Clin. Oncol.* 14:737–744 [1996]). However, the presence of circulating endogenous ECD in the serum of normal individuals, and often at high levels in breast cancer patients, interferes with the assay by competing with ECD coated on microtiter ELISA plates for binding to serum HERCEPTIN®. The net result is underestimation of circulating HERCEPTIN® levels in serum. Therefore, there is a significant clinical need to improve the assay for accurately measuring serum level of anti-HER2 antibodies in the presence of circulating endogenous HER2 ECD.

SUMMARY OF THE INVENTION

The invention discloses a general method for accurately determining the amount of an analyte in a fluid sample in the presence of an interfering substance. A method disclosed herein circumvents the problem of underestimation, as a result of the presence of the interfering substance, without introducing additional steps of prior treatment of samples, thus retaining the simplicity and convenience of immunoassay. The method is illustrated by disclosure of an improved ELISA method for accurate measurement of serum HERCEPTIN® levels in the presence of circulating HER2 ECD that binds to HERCEPTIN® and interferes in quantitation, but is not limited to the ELISA format or to the determination of HERCEPTIN® levels.

In one aspect, the present invention concerns a method for accurate determination of the amount of an analyte in a fluid sample in the presence of an interfering substance comprising: (a) providing a solid surface dual-coated with a first antibody directed against the analyte and a second antibody directed against the interfering substance; (b) contacting the dual-coated surface with the fluid sample, whereby the first antibody binds the free analyte and the second antibody binds the interfering substance bound to the analyte; and (c) determining the total amount of the free analyte and the analyte bound to the interfering substance. The total amount of the analyte may be determined by contacting the product of step (b) above with a detectably labeled secondary antibody recognizing the analyte. Finally, quantitation of the analyte may be achieved by comparing the signal in the sample with a standard curve generated using various concentrations of the purified analyte in place of the fluid sample in step (b).

The first and the second antibodies may be polyclonal or monoclonal antibodies, including antibody fragments. The epitope on the analyte recognized by the secondary antibody is different both from the epitope recognized by the first antibody and from the epitope recognized by the interfering substance. The detection label conjugated to the secondary antibody can be an enzyme such as peroxidase, for instance horseradish peroxidase, but other suitable enzymes, for example alkaline phosphatase, may also be used. A substrate for the enzyme conjugated with the secondary antibody is used as an indicator. For example, ortho-phenylene diamine (OPD) can be used to detect the presence of peroxidase. Any suitable substrate, which when acted upon by the enzyme is converted into a product whose absorption maxima is different from that of the substrate (in visible or UV range), can be used as an indicator to monitor the enzymatic activity. The analyte, which is a subject of quantitation as described herein, could be a polypeptide. The quantitation of a receptor, with interfering substance being a ligand for the receptor, is also within the scope of the invention.

In another aspect, the invention provides a method for accurately determining the amount of an antibody in a fluid sample in the presence of an interfering substance capable of binding to the antibody, comprising: (a) providing a solid surface dual-coated with a first antibody recognizing the free antibody and a second antibody recognizing the interfering substance when bound to the antibody; (b) contacting the dual-coated surface with the fluid sample, whereby the first antibody binds the free antibody and the second antibody binds the interfering substance bound to the antibody; and (c) determining the total amount of the free antibody and the antibody bound to the interfering substance. The total amount of the antibody is determined by contacting the product of step (b) with a detectably labeled secondary antibody. Finally, quantitation of the antibody is achieved by comparing the signal in the sample with a standard curve generated by using various concentrations of the purified antibody in place of the fluid sample in step (b). In a preferred embodiment, the antibody recognizes an antigen and the interfering substance is a polypeptide derived from the antigen. The antigen may be a receptor and the interfering polypeptide may be a fragment derived from the receptor. The secondary antibody is raised against an immunoglobulin derived from the same species as the analyte antibody.

The first and the second antibodies may be polyclonal or monoclonal antibodies, including antibody fragments. The secondary antibody recognizes the epitope on the analyte antibody different both from the epitope recognized by the first antibody and from the epitope recognized by the interfering substance. The detection label conjugated to the secondary antibody can be an enzyme such as peroxidase, for instance horseradish peroxidase, but other suitable enzymes, for example alkaline phosphatase, may also be used. A substrate for the enzyme conjugated with the secondary antibody is used as an indicator. For example, ortho-phenylene diamine (OPD) can be used to detect the presence of peroxidase. Any suitable substrate, which when acted upon by the enzyme is converted into a product whose absorption maxima is different from that of the substrate (in visible or UV range), can be used as an indicator to monitor the enzymatic activity.

In a preferred embodiment, the invention discloses by the way of illustration, a method of accurately determining the levels of an anti-HER2 antibody in the presence of an interfering substance, an extracellular domain (ECD) of HER2 oncoprotein. The anti-HER2 antibody could be a polyclonal or a monoclonal antibody or a fragment derived therefrom. The monoclonal anti-HER2 antibody may be a murine monoclonal antibody such as 4D5 or a humanized version of recombinant 4D5. In a particularly preferred embodiment, the humanized version of recombinant 4D5 anti-HER2 antibody is HERCEPTIN®. The method uses the first antibody recognizing anti-HER2 such as HERCEPTIN®, and the second antibody recognizing HER2 ECD at an epitope different from that recognized by the anti-HER2 antibody. The first antibody recognizing HERCEPTIN® does not significantly cross-react with human IgG. The second antibody against ECD could be a polyclonal or a monoclonal antibody, such as 7C2. The first antibody that recognizes HERCEPTIN® may be a monoclonal antibody such as AMER5. The fluid sample in which the accurate determination of the level of anti-HER2 antibody is sought may be a serum or plasma derived from a cancer patient undergoing anti-HER2 therapy. In a a particularly preferred embodiment, the cancer patient may be suffering from a cancer overexpressing HER2 such as breast cancer.

In a different aspect, the invention provides a method for determining the amount of an analyte in a fluid sample in the presence of an interfering substance, comprising: (a) providing a solid surface dual-coated with a first capture reagent recognizing the free analyte and a second capture reagent recognizing the interfering substance when bound to the analyte; (b) contacting the dual-coated surface with the fluid sample, whereby the first capture reagent binds the free analyte and the second capture reagent binds the interfering substance bound to the analyte; and (c) determining the total amount of the free analyte and the analyte bound to the interfering substance.

In a still different aspect, the invention provides a method for determining the amount of an analyte in a fluid sample in the presence of an interfering substance, comprising: (a) providing a first antibody recognizing the free analyte and a second antibody recognizing the interfering substance when bound to the analyte; (b) contacting the first antibody and the second antibody with the fluid sample, whereby the first antibody binds the free analyte and the second antibody binds the interfering substance bound to the analyte; and (c) determining the total amount of the free analyte and the analyte bound to the interfering substance. The determination of the total amount of the analyte may be performed by fluorescence resonance energy transfer (FRET).

In another aspect, the invention provides a kit for accurately determining the amount of an anti-HER2 antibody in serum or plasma in the presence of HER2 ECD, comprising: (a) a solid surface coated with a first antibody recognizing the free anti-HER2 antibody and a second antibody recognizing the HER2 ECD when bound to the anti-HER2 antibody; and (b) a detectably labeled secondary antibody recognizing the anti-HER2 antibody at an epitope different from that recognized by the first antibody as well as different from that recognized by the HER2 ECD. The solid surface of the kit may be configured in form of a test tube, a well, a bead, a rod, or a strip, and may be composed of glass, plastic, or paper. The plastic may be made up of polystyrene or polyacylate. The anti-HER2 antibody may be a murine monoclonal antibody such as 4D5 or a humanized and a recombinant version of it such as HERCEPTIN®. The first antibody coated on solid surface recognizes a murine monoclonal antibody against HER2 such as 4D5 or a humanized and a recombinant version of 4D5 such as HERCEPTIN®. The anti-HERCEPTIN antibody may be a monoclonal antibody such as AMER5 or a fragment of it. The second antibody recognizing HER2 ECD could be a polyclonal or a monoclonal antibody or a fragment derived therefrom. The monoclonal antibody against HER2 ECD could be 7C2 or a fragment derived therefrom. The serum or plasma sample used for the determination of anti-HER2 antibody may be derived from a cancer patient undergoing anti-HER2 therapy such as a patient suffering from HER2-overexpressing breast cancer. In a preferred embodiment, the solid surface is a surface of wells of a microtiter plate.

Finally, the invention also provides a microtiter plate for accurately determining the amount of an anti-HER2 antibody in serum or plasma in the presence of HER2 ECD, comprising: (a) a first antibody recognizing the free anti-HER2 antibody and a second antibody recognizing the HER2 ECD when bound to the anti-HER2 antibody; and (b) wherein the first and the second antibodies are coated on the surface of the microtiter plate.

DETAILED DESCRIPTION OF THE
PREFERRED EMOBODMENT

Definitions

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y., 1994). Many general terms and concepts related to the present invention are described in Harlow and Lane, *Using Antibodies: A Laboratory Manual*, Cold Spring Harbor Laboratory Press (Cold Spring Harbor, N.Y., 1999). One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "analyte" as used herein refers to a substance being analyzed for qualitative detection or quantitation estimation using an appropriate assay.

The term "interfering substance" as used herein refers to a substance which, when present in a sample along with an analyte, interferes with an accurate determination of the amount of the analyte in any way including, but not limited to, by binding to and thus masking an epitope on the analyte and preventing it from being recognized by the antibody against the analyte used in the method. Such interference results in underestimation of the analyte.

The term "solid surface" refers to a solid surface used in the assay as described in the invention for coating antibodies in order to capture an analyte present in a sample. The solid surface thus provides a solid phase for immunological reactions to take place between components of the sample and various reagents during various steps in the assay, and it serves to isolate and concentrate reacting species from a fluid sample. The solid surface may be in various configuration such as a test tube, a well, a bead, a rod, or a strip, and may be composed of materials such as glass, plastic, or paper. The plastic may be made up of polystyrene or polyacrylate or any other suitable material.

The term "fluid sample" refers to a sample that is liquid in nature. The fluid sample used for the assay described herein is often, but does not have to be, a biological fluid such as serum, plasma, peritoneal fluid, cerebrospinal fluid, lymph and so forth.

The terms "ErbB2", "ErbB2 receptor", and "HER2" are used interchangeably, and, unless otherwise indicated, refer to a native sequence ErbB2 human polypeptide, or a functional derivative thereof. The term "ECD" or "extracellular domain" refers to a sequence on the N-terminal end of HER2 protein that is present on the outer face of the cell membrane.

The term "capture reagent" refers to reagents are used in the assay in place of antibodies to capture an analyte or an interfering substance. Any reagent that possesses a high degree of specificity and affinity for the analyte or the interfering substance can be used as capture reagents. For example, a specific receptor or a ligand can be used for the purpose, and such capture reagents are well within the scope of the instant invention.

The term "immunoassay" refers to an assay that utilizes a high degree of antigenic specificity and affinity of an antibody for an antigen for a qualitative detection or a quantitative estimation of an antigen. In solid phase immunoassays, immunological reactions during the assay take place on a solid phase. One advantage of solid phase assay is its ability to isolate reacting components from a fluid sample and increase concentration of interacting species in a local micro-environment. Another advantage is a convenience of washing away other unnecessary components of fluid sample at every step. One of the popular formats for performing such a solid phase immunoassay is Enzyme-Linked Immunosorbent Assay or "ELISA." In a simple variation of ELISA used for detection or estimation of an analyte, a specific antibody raised against the analyte is coated on a solid surface such as wells in microtiter plates. When a fluid sample is contacted with such antibody-coated plate, the analyte present in sample specifically binds to the immobilized antibodies and thus separated from other components of the sample. The immobilized analyte on the plate is then detected by incubating with a secondary antibody directed against the same analyte but recognizing an epitope different from that recognized by the antibody coated on the solid surface. The secondary antibody is usually detectably labeled with, for instance, an enzyme, which is conveniently detected by incubating with a solution containing substrate for the enzyme. The product of the enzymatic reaction is measured at an appropriate wavelength in an ELISA reader. Finally, the quantitation of the analyte present in a sample is achieved by comparing it with readings obtained using known various amounts of a purified analyte.

The term "quantitative" refers to an attribute of an assay such as ELISA that seeks to accurately determine the amount of a particular substance in a sample. The term "receptor" refers to a cell membrane protein which binds to a specific ligand and transduces signal intracellularly with defined physiological consequences. The term as used herein also includes receptors that are shed by cells into surrounding medium such as blood, lymph, cerebrospinal fluid etc. The term "ligand" refers to a biological compound that specifically interacts with a cognate receptor on cell membrane of responsive cell. It includes a variety of functional classes such as hormones, cytokines, lymphokines, chemokines etc. A ligand may be macromolecular in nature such as protein or a small molecular weight compound such as glucocorticoids and steroids. The term "epitope" refers to a small and distinct part of the antigen that acts as an antigenic determinant and that is specifically recognized by an antibody. It is also sometimes used to refer to a distinct region or domain of a polypeptide involved in interaction with other polypeptides.

The term "antibody" herein is used in the broadest sense and specifically covers intact monoclonal antibodies, polyclonal antibodies, multispecific antibodies (e.g. bispecific antibodies) formed from at least two intact antibodies, single chain antibodies and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624–628 (1991) and Marks et al., *J. Mol. Biol.*, 222:581–597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851–6855 (1984)). Chimeric antibodies of interest herein include primatized antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Riechmann et al., *Nature* 332:323–329 (1988); and Presta, *Curr. Op. Struct. Biol.* 2:593–596 (1992).

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies.

A "HER2-expressing cancer" is one comprising cells which have HER2 protein present at their cell surface. A "HER2-expressing cancer" is one which produces sufficient levels of HER2 at the surface of cells thereof, such that an anti-HER2 antibody can bind thereto and have a therapeutic effect with respect to the cancer.

A cancer "characterized by excessive activation" of HER2 is one in which the extent of HER2 activation in cancer cells significantly exceeds the level of activation of that receptor in non-cancerous cells of the same tissue type. Such excessive activation may result from overexpression of HER2 and/or greater than normal levels of a HER2 ligand available for activating the HER2 in the cancer cells. Such excessive activation may cause and/or be caused by the malignant state of a cancer cell.

A cancer which "overexpresses" a HER2 is one which has significantly higher levels of HER2, at the cell surface thereof, compared to a noncancerous cell of the same tissue type. Such overexpression may be caused by gene amplification or by increased transcription or translation. HER2 overexpression may be determined in a diagnostic or prognostic assay by evaluating increased levels of the HER2 protein present on the surface of a cell (e.g. via an immunohistochemistry assay; IHC). Alternatively, or additionally, one may measure levels of HER2-encoding nucleic acid in the cell, e.g. via fluorescent in situ hybridization (FISH; see WO98/45479 published October, 1998), Southern blotting, or polymerase chain reaction (PCR) techniques, such as real time quantitative PCR (RT-PCR). One may also study HER2 overexpression by measuring shed antigen (e.g., HER2 extracellular domain) in a biological fluid such as serum (see, e.g., U.S. Pat. No. 4,933,294 issued Jun. 12, 1990; WO91/05264 published Apr. 18, 1991; U.S. Pat. No. 5,401, 638 issued Mar. 28, 1995; and Sias et al. *J. Immunol. Methods* 132: 73–80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which is "not characterized by overexpression of the HER2" is one which, in a diagnostic assay, does not express higher than normal levels of HER2 compared to a noncancerous cell of the same tissue type.

A "small molecule" is defined herein to have a molecular weight below about 500 Daltons.

Description of Preferred Embodiments

The present invention addresses the long-felt unmet need of circumventing a frequent problem in the use of immunoassays in accurately estimating the amount of an analyte in a fluid sample. The problem is caused by the presence of an interfering substance in a sample that competes with the analyte for binding to the antibodies against the analyte. This interference leads to underestimation of the analyte and compromises the quantitative aspect of an immunoassay. Although a sample can be pretreated to remove the interfering substance, for example by suitable chromatography, the additional steps make the assay time consuming, cumbersome and also leads to loss of sample. The present invention discloses a solid phase immunoassay with the use of two antibodies for coating the solid phase. The first antibody recognizes the free analyte whereas the second antibody recognizes the interfering substance complexed with the analyte. The introduction of the second antibody thus allows estimation of the bound analyte which is otherwise not accounted for in the immunoassay employing only one antibody recognizing the analyte. The strategy effectively eliminates the problem of underestimation as a result of the presence of the interfering substance. Reagents other than antibodies can also be used for capture of an analyte. For example, a specific receptor or a ligand can be substituted in the place of antibodies, and these capture reagents are well within the scope of the invention.

The solid surface used for coating antibodies may be in various configurations such as a test tube, a well of microtiter plate, a bead, a rod, or a strip. Similarly, the solid surface may be made up of a wide variety of materials such as glass, plastic or paper. The examples of the most widely used plastic material are polystyrene and polyacrylate. However, any suitable material in any suitable and convenient configuration can be used for coating the antibodies and is well within the scope of the disclosed invention. The sample for analysis may be a biological sample such as serum or plasma.

The analyte, free as well as bound to interfering substance, captured on the solid surface by the use of aforementioned two antibodies is then detected by incubating with a secondary antibody also recognizing the analyte but directed against the epitope different both from the epitope recognized by the coated anti-analyte antibody and from the epitope recognized by the interfering substance. The secondary antibody is detectably labeled such as by conjugating with a suitable enzyme, for instance horseradish peroxidase or alkaline phosphatase. The activity of the enzyme is estimated by incubating with a suitable substrate. Finally, quantitation of the analyte is achieved by comparing the enzyme activity obtained in a sample with a standard curve generated using various concentration of the purified analyte. The secondary antibody can also be detectably labeled using a variety of means including, but not limited to, fluorescent, radioactive or chemiluminescent tags. For example, some of the widely used fluorochromes that are used for qualitative and quantitative immunoassays are fluorescein, rhodamine, Texas Red, and phycoerythrin. A radioactive tag that is most frequently used to detectably label the secondary antibody is radioactive iodine ($^{125}$I). As it will be apparent to a person skilled in the art that any variation on a theme is possible. For example, in order to enhance the sensitivity of the detection method, a biotinylated secondary antibody may be used followed by an enzyme conjugated to avidin such as streptavidin. This step serves to considerably amplify the signal since every molecule of avidin binds 4 molecules of biotin. Moreover, the affinity of avidin for biotin is extremely high, of the order of $10^{-12}$ M. The first and the second antibodies used for coating on solid surface may be polyclonal or monoclonal antibodies. The analyte may be a polypeptide. The invention specifically covers the estimation of a receptor, wherein the interfering substance is a ligand for the receptor.

In an alternative embodiment, the method can be practiced in a bi-phasic manner such as the capture step carried out entirely in fluid phase, followed by separation of the captured analyte complexed with the capture reagent on a solid phase. For example, a biotinylated antibody or any other capture reagent can be used in liquid phase to capture the analyte, and the resultant complex can then be applied to a solid phase coated with streptavidin. The immobilized complex can then be detected as described. Yet another variation is the use of precipitation to collect the complexed analyte.

It is also possible to use entirely fluid phase to carry out the assay. For example, fluorescence resonance energy transfer (FRET) can be employed in which a tag on the two primary or capture antibodies transfer energy to a tag on the secondary antibody when these are brought close together by ligand (or ligand-interfering molecule) interaction. FRET is a phenomenon that occurs when two fluorophores are in sufficient proximity (<100 A°) and an appropriate relative orientation such that an excited fluorophore (donor) can transfer its energy to a second, longer wavelength fluorophore (acceptor) in a non-radiative manner. Thus, excitation of the donor can produce light emission from the acceptor, with attendant loss of emission from the donor. The resonance conditions necessary for this process dictate that the fluorescence emission spectra of the donor overlap with the absorption spectra of the acceptor molecule. The versatile nature of FRET has made it a valuable tool in a variety of applications ranging from structural analysis of proteins, nucleic acids and carbohydrates, molecular interactions between proteins and/or nucleic acids, diagnostic assays, fluorescence imaging in live cells, and high throughput screening assays in drug discovery (reviewed in Clegg, *Curr. Opin. Biotech.* 6: 103–110 [1995]; Bastiaens and Squire, *Trends Cell Biol.* 9: 48–52 [1999]).

In a preferred embodiment, the assay of the invention is used for accurate quantitation of an antibody in a sample in the presence of an interfering substance that binds to the antibody. The interfering substance in this case is usually a polypeptide fragment, derived from the cognate antigen, sharing the epitope recognized by the analyte antibody. Among the two antibodies used for coating solid substrate, one antibody binds to the free antibody and the other antibody binds to the interfering substance bound to the antibody. The secondary antibody, conjugated with a suitable enzyme, is selected so as to recognize the epitope on the analyte antibody which is different both from the epitope recognized by the coated anti-analyte antibody and from the epitope recognized by the anti-interfering substance antibody. The secondary antibody is raised against an immunoglobulin derived from the same species as the analyte antibody.

In a particularly preferred embodiment, the strategy is illustrated by its application to the accurate estimation of the amount of circulating HERCEPTIN® in serum or plasma of cancer patients undergoing HERCEPTIN® therapy. One of ordinary skill in the art would understand that the estimation of any anti-HER2 antibodies, polyclonal, monoclonal, humanized or recombinant, is well within the scope of the disclosed strategy. As described earlier, HERCEPTIN® has been successfully used in the treatment of breast cancer. However, the level of serum HERCEPTIN® should be maintained at 5–10 µg/ml during the therapy in order to effectively inhibit the growth of HER2 overexpressing breast cancer cells. Monitoring the level of serum HERCEPTIN® is thus crucial in the course of HERCEPTIN® therapy. A specific ELISA for the detection and quantitation of HERCEPTIN®, using HER2 extracellular domain (ECD) as a capture reagent, has been developed (Baselga et al., *J. Clin. Oncol.* 14:737–744 [1996]). However, the presence of circulating endogenous ECD in the serum of normal individuals, and often at high levels in breast cancer patients, interferes with the assay by competing with ECD coated on microtiter ELISA plates for binding to serum HERCEPTIN®. The net result is under-estimation of circulating HERCEPTIN® levels in serum. The assay disclosed herein eliminates the problem of interference by utilizing two antibodies for coating on solid surface. One of them recognizes free HERCEPTIN®, and the other recognizes ECD bound to HERCEPTIN®. The anti-HERCEPTIN® antibody used may be polyclonal or monoclonal. In a preferred embodiment, a monoclonal antibody such as AMER5 may be used for the assay. Similarly, a polyclonal or monoclonal antibody against ECD may be used to capture ECD complexed with HERCEPTIN®. In a preferred embodiment, a monoclonal antibody such as 7C2 may be used as an anti-ECD antibody.

The assay may be used for the estimation of circulating anti-HER2 antibodies in serum of patients receiving anti-HER2 therapy. The patients include those suffering from HER2 overexpressing cancer such as breast cancer.

The present invention also discloses a kit for accurately determining the amount of circulating anti-HER2 antibody in serum or plasma in the presence of circulating HER2 ECD. The kit comprises a solid surface dually coated with an antibody recognizing anti-HER2 antibody and an antibody recognizing HER2 ECD. The kit also includes a secondary antibody recognizing anti-HER2 antibody at the epitope different both from the epitope recognized by the coated anti-HER2 antibody and from the epitope recognized by the coated anti-HER2 ECD antibody. The secondary antibody is detectably labeled, for example by conjugating with any suitable enzyme such as horseradish peroxidase and alkaline phosphatse. The kit may be used in the estimation of any anti-HER2 antibody whether polyclonal, monoclonal, humanized or recombinant. In a preferred embodiment, the kit is used for estimating circulating HERCEPTIN®. The coated antibody that recognizes anti-HER2 antibody may be polyclonal or monoclonal. In a preferred embodiment, monoclonal antibody recognizing HERCEPTIN® is AMER5. Similarly, a polyclonal or monoclonal antibody recognizing HER2 ECD may be used for coating. In a preferred embodiment, a monoclonal antibody such as 7C2 may be used for the purpose.

The invention disclosed herein also provides a microtiter plate dually coated with an antibody recognizing anti-HER2 antibody and an antibody recognizing HER2 ECD. The microtiter plate may be made of plastic such as polystyrene or polyacrylate. The dually-coated microtiter plate may be used for the estimation of any anti-HER2 antibody, polyclonal, monoclonal, humanized or recombinant, in the presence of interfering substance such as HER2 ECD. In a preferred embodiment, the microtiter plate is used for the estimation of HERCEPTIN®, preferably in serum or plasma of patients receiving anti-HER2 therapy for the treatment of cancer, preferably overexpressing HER2 such as breast cancer. The coated antibody that recognizes anti-HER2 antibody may be polyclonal or monoclonal. In a preferred embodiment, monoclonal antibody recognizing HERCEPTIN® is AMER5. Similarly, a polyclonal or monoclonal antibody recognizing HER2 ECD may be used for coating. In a preferred embodiment, a monoclonal antibody such as 7C2 may be used for the purpose.

Further details of the invention are provided in the following non-limiting examples.

EXAMPLES

Example 1

Improved ELISA for Quantitative Estimation of HERCEPTIN® in Presence of ECD

Figure 1:
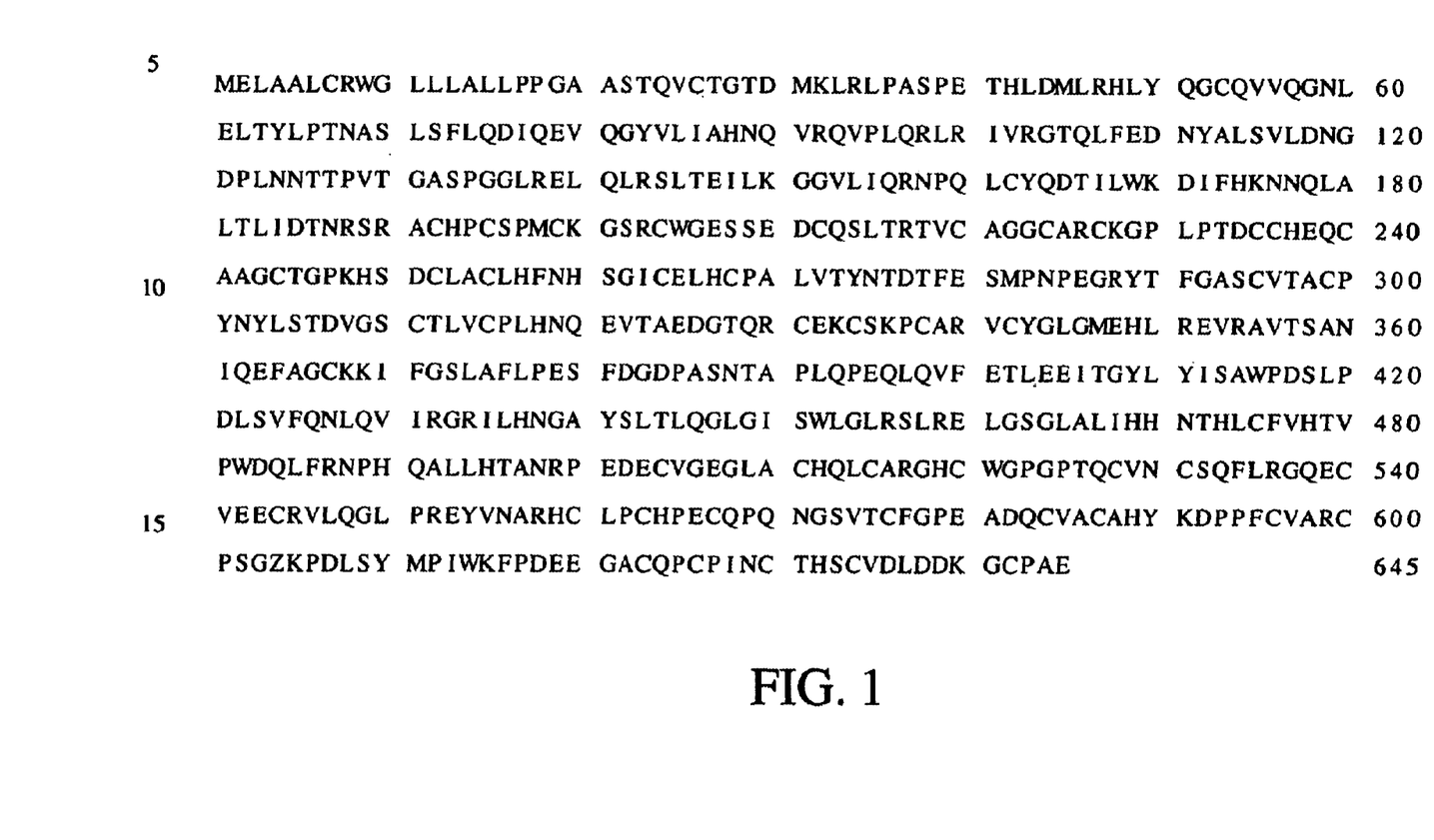
FIG. 1 shows amino acid sequence of the extracellular domain (ECD) of HER2 receptor (SEQ ID NO: 1). Amino acid residues 1–21 constitute a signal peptide.

FIG. 1 shows amino acid sequence of the extracellular domain (ECD) of HER2 receptor (SEQ ID NO: 1). Amino acid residues 1–21 represent the N-terminal signal peptide. Recombinant ECD (rECD, p105$^{HER2}$) was produced in CHO cells, immuno purified on an anti-HER2 column, removing any contamination by that MAb on a protein A column, followed by DEAE ion exchange chromatography. It ran as a homogenous band of apparent molecular weight 110–115 kDa by SDS-PAGE. Mass concentration was determined by amino acid analysis. A recombinant humanized version of the murine anti-ErbB2 antibody 4D5, also known as huMAb4D5-8, rhuMAb HER2 or HERCEPTIN® is described in U.S. Pat. No. 5,821,337. HERCEPTIN® was expressed in CHO cells and purified as described (Baselga et al., *J. Clin. Oncol.* 14:737–744 [1996]; Pegram et al, *Am. Assoc. Cancer Res* 38: A4044 [1997]; U.S. Pat. No. 5,821, 337). Anti-HER2 (7C2) antibody was constructed as a humanized monoclonal antibody in the IgG1 framework, based on the 4D5 murine MAb, as described by Carter et al. (Proc. Natl. Acad. Sci. USA 89: 4285 [1992]). It was expressed in CHO cells.

Murine MAbs to HERCEPTIN® (such as AMER5) were produced and characterized by standard methods. ERCEPTIN® pressed purified purified frmo CHO cells was used to immunize mice. Spleen cells from immunized mice were fused with myeloma cells, the hybrid cells were selected, cloned and screened for aitbodies which specifically recognize HERCEPTIN®.

One of the problems immunoassays often suffer from is the interference by naturally occurring substances which compete with the target antigen (the analyte) for binding to the antibodies and thereby blocking detection. It could mean loss of detection in the qualitative assays, and underestimation in the quantitative assays. In order to monitor the level of serum HERCEPTIN®, which is crucial for the successful HERCEPTIN® therapy of breast cancer, an ELISA was developed. This assay uses recombinant extracellular domain (ECD) of HER2 for coating microtiter ELISA plates to capture HERCEPTIN®, and peroxidase-conjugated goat anti-human IgG Fc for detection. However, circulating endogenous ECD is present in normal individuals, often at higher levels in cancer patients (Mielke et al, *Gynaecol. Endosc.* 6: 237–241 [1997]; Yamauchi et al., *J. Clin. Oncol.* 15: 2518–2525 [1997]; Fehm et al., *Oncology* 55: 33–38 [1998]). This circulating ECD competes at the capture step in the assay, and experiments show that recovery of HERCEPTIN® is compromised at mass ratios of HERCEPTIN®:ECD less than 10. A strategy was devised and optimized to circumvent this problem. The present invention discloses an ELISA that uses a dual coat of a MAb to HERCEPTIN® to capture free HERCEPTIN®, and a MAb to ECD that captures HERCEPTIN® complexed with ECD. The resulting assay quantitatively measures HERCEPTIN® in the presence of 200-fold weight excess of ECD.

Single coat ELISA for HERCEPTIN® in human serum.

The assay was described previously (Baselga et al., *J. Clin. Oncol.* 14:737–744 [1996]). For quantitating HERCEPTIN® in blood, 100 µl of ECD at 0.5 µg/ml in 0.05 M sodium carbonate buffer, pH 9.5, was bound to wells of microtiter plates. After overnight incubation at 4° C., plates were washed 3 times with Wash Buffer (PBS containing 0.05% Tween-20 and 0.01% Thimerosal) and blocked for 1 hour with Assay Diluent (Wash Buffer containing 0.05% BSA) on an orbital shaker. After blocking, plates were washed 3 times and 100 µl samples or control, diluted in Assay Diluent, were added to duplicate wells and incubated for 1 to 2 hours at room temperature while shaking. After washing, 100 µl peroxidase-conjugated goat anti-human IgG Fc (1:1000 in Assay Diluent) was added to wells for 1 to 2 hours followed by washing. Color was developed by addition of 100 µl ortho-phenelyne diamine (OPD) substrate solution (5 mg in 12.5 ml 4 mM $H_2O_2$ in PBS) and incubation for about 20 min. The reaction was stopped with 0.1 ml 2M sulphuric acid and read at 492 nm with subtraction of background at 405 nm.

Dual coat ELISA for HERCEPTIN®

Various concentrations of coating reagents and different buffers were tested as described in Results. The optimized assay thus developed was performed using 100 µl of a solution containing 10 µg/ml each of AMER5 and 7C2 MAbs for coating on microtiter ELISA plates. All the other steps such as blocking and washing were same as above for the single coat ELISA.

Results

Interference by ECD in a Single Coat ELISA for Quantitation of Serum Levels of HERCEPTIN®

Figure 2:
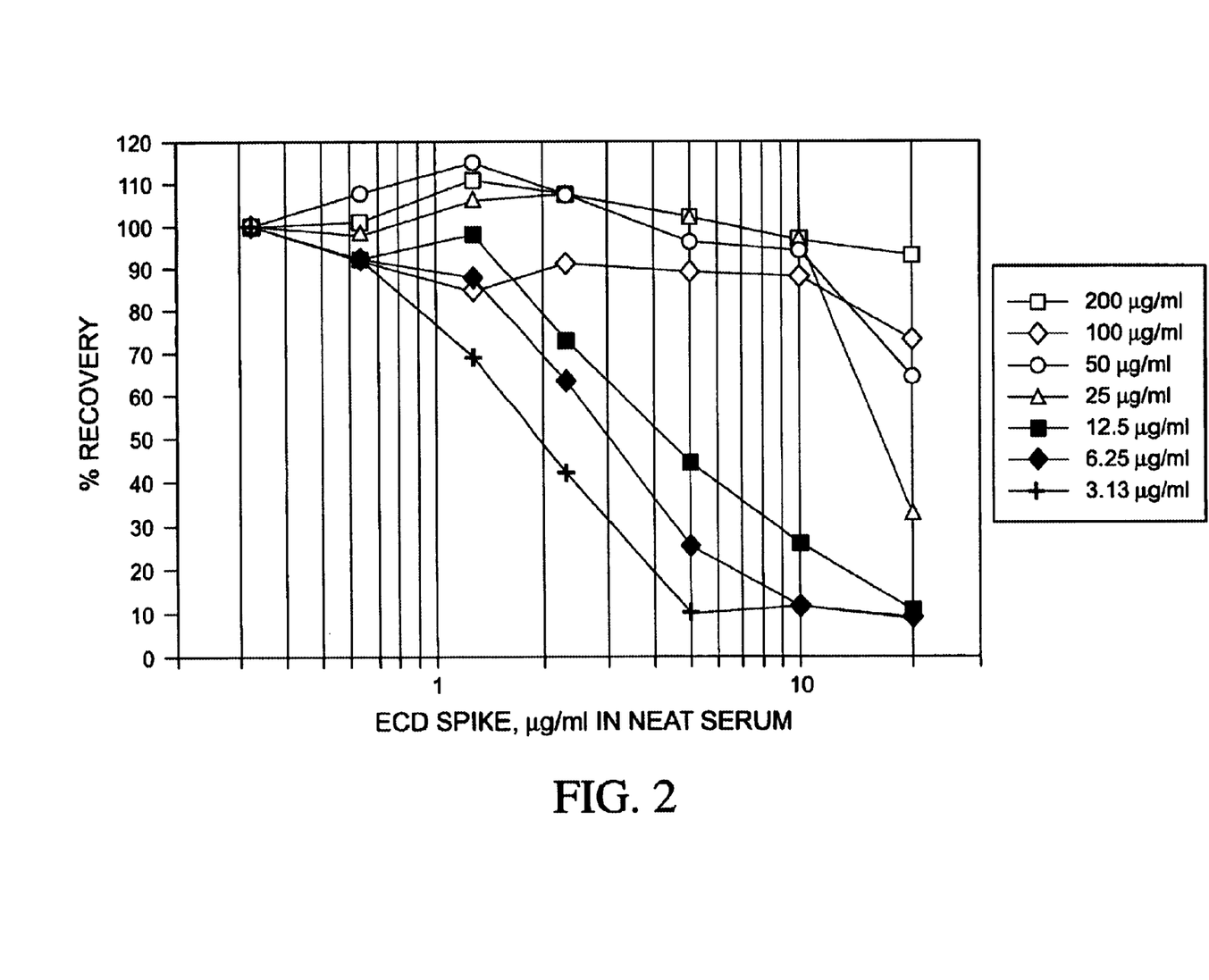
FIG. 2 shows interference, by added recombinant ECD, in the quantitative estimation of HERCEPTIN® by anti-HERCEPTIN® antibodies using ELISA.

In order to monitor serum level of HERCEPTIN® in breast cancer patients undergoing HERCEPTIN® therapy, an ELISA was developed. The assay uses the target antigen, HER2 ECD as a coat to capture, and peroxidase-labeled goat anti-human IgG Fc fragment to detect the antigen. It requires a minimum of 1/100 dilution of serum and has a sensitivity corresponding to 39 ng/ml neat serum. However, the presence of circulating endogenous ECD, detected in breast cancer patients at concentrations approaching 1 µg/ml serum (Fehm et al., *Oncology* 55: 33–38 [1998]), is likely to interfere with the detection of HERCEPTIN® by competing with the coated ECD in the assay plate. This possibility was examined by adding various concentrations of rECD into samples containing various concentrations of HERCEP- TIN® in a matrix format. More specifically, normal human serum was spiked with concentrations of anti-HER2 from 3.13 to 200 µg/ml. ECD was added to replicate samples at concentrations from 0.62 to 20 µg/ml. The samples were diluted a minimum of 1:100 in Assay Diluent and submitted to the assay in duplicate in two-fold dilutions over the valid assay range. As shown in FIG. 2, ECD at concentrations above 1 µg/ml neat serum inhibited detection of moderate levels of anti-HER2 (3.13 to 12.5 µg/ml) by more than 20%. High anti-HER2 levels up to 100 µg/ml were inhibited by ECD at 20 µg/ml. When the sample incubation was extended to overnight at room temperature, less but significant interference by ECD was also seen.

As shown in FIG. 2, detection of 5–10 µg/ml of HERCEPTIN® was inhibited by more than 20% by ECD concentrations at or above 2.5 µg/ml (FIG. 2). In clinical setting, patients are administered weekly doses and the target is to maintain serum levels of 5–10 µg/ml of HERCEPTIN® by repeat doses. Therefore, circulating, endogenous ECD concentrations above 2.5 µg/ml could significantly inhibit detection of 5–10 µg/ml of HERCEPTIN® that is sought to be maintained in clinical practice. The interference by circulating ECD would thus lead to underestimation of serum HERCEPTIN® levels.

Screening of "Anti-idiotypic" MAbs to HERCEPTIN® as ELISA Coats

Since circulating ECD could interfere in the established antigen/antibody EIA for HERCEPTIN®, an alternative assay that would accurately quantitate HERCEPTIN® in the presence of ECD was developed. An attempt was made to find a reagent antibody that could bind to anti-HER2 and not be blocked by ECD. Ten murine MAbs to HERCEPTIN® that had been identified as "anti-idiotypic" based on binding to HERCEPTIN® but not to other humanized anti-HER2 antibodies such as E25, directed to the human IgE, were examined. An antibody that would bind to HERCEPTIN® in the presence or absence of ECD, but not to normal serum IgG, was sought. Such an antibody could be used to coat to capture HERCEPTIN® in serum. These anti-idiotypic antibodies were coated individually at 1 µg/ml and the plates were blocked as in FIG. 2. Anti-HER2 was added as sample at 3.13 µg/ml in neat serum, incubated 1 h or overnight, followed by detection as in FIG. 2. The OD values for detection of anti-HER2 alone (i.e. in the absence of ECD), with ECD at 20 µg/ml, and for the blank with no anti-HER2 or ECD are presented in Table 1.

TABLE 1

| Incubation | Coat | HER2 @ 3.13 µg/ml | | | Blank % recovery |
| | | ECD @ 20 µg/ml | No ECD | Blank | |
|---|---|---|---|---|---|
| 1 h | AMER1 | 1.770 | 1.661 | 1.706 | — |
| O/N | AMER1 | 1.381 | 1.257 | 1.279 | — |
| 1 h | AMER11 | 0.781 | 1.175 | 0.684 | 20 |
| O/N | AMER11 | 0.775 | 1.109 | 0.725 | 13 |
| 1 h | AMER13 | 0.418 | 1.230 | 0.327 | 10 |
| O/N | AMER13 | 0.623 | 1.142 | 0.484 | 21 |
| 1 h | AMER15 | 0.497 | 1.262 | 0.403 | 11 |
| O/N | AMER15 | 0.590 | 1.094 | 0.475 | 19 |
| 1 h | AMER17 | 0.482 | 1.213 | 0.370 | 13 |
| O/N | AMER17 | 0.712 | 1.221 | 0.568 | 22 |
| 1 h | AMER18 | 0.446 | 1.203 | 0.352 | 11 |
| O/N | AMER18 | 0.636 | 1.150 | 0.495 | 22 |
| 1 h | AMER20 | 0.477 | 1.246 | 0.371 | 12 |
| O/N | AMER20 | 0.671 | 1.210 | 0.550 | 18 |
| 1 h | AMER5 | 0.585 | 1.349 | 0.293 | 28 |
| O/N | AMER5 | 0.938 | 1.197 | 0.404 | 67 |
| 1 h | AMER9 | 0.889 | 1.408 | 0.786 | 17 |

TABLE 1-continued

| Incubation | Coat | HER2 @ 3.13 µg/ml | | | Blank % recovery |
| | | ECD @ 20 µg/ml | No ECD | Blank | |
|---|---|---|---|---|---|
| O/N | AMER9 | 0.912 | 1.340 | 0.795 | 21 |
| 1 h | AMER10 | 0.686 | 0.993 | 0.539 | 32 |
| O/N | AMER10 | 0.699 | 0.893 | 0.617 | 30 |

Some MAbs, such as AMER5 had relatively low OD values with no anti-HER2 (blank) and high signals with anti-HER2 (OD 1.349 for 1 h incubation), but the presence of ECD at 20 µg/ml strongly inhibited the response (OD 0.585). Subtracting the background blank values from these data shows that recovery of anti-HER2 was only 28% of expected. Other MAbs gave very high background in 1% normal human serum in the absence of anti-HER2, e.g. AMER1 with 1 h sample incubation had a blank OD of 1.706. This high background is presumably a cross-reaction between the coat MAb and some component in normal human serum, disqualifying the usefulness of these MAbs. No "anti-idiotype" MAb to anti-HER2 was found satisfactory as a coat reagent to capture anti-HER2 in the presence of ECD.

Use of a Capture MAb to ECD to Detect HERCEPTIN® Bound to ECD

Since an alternative MAb sandwich format could not be developed, another alternative for quantitating HERCEPTIN® in the presence of serum ECD was investigated. A mouse MAb to an epitope on ECD different from that recognized by the therapeutic antibody (i.e. HERCEPTIN®) could be used for coating to capture ECD, including ECD molecules that carried HERCEPTIN® antibody. The HERCEPTIN® thus captured could be measured by a suitable detection antibody to form an assay for HERCEPTIN® bound to ECD.

Development of a Dual Coat ELISA

A possibility of using a dual coating to detect total HERCEPTIN® in a serum sample that also contained ECD was examined. One component of the coating would capture HERCEPTIN® bound to ECD. Whereas the other component would capture free HERCEPTIN®. A mouse MAb, 7C2, to an epitope on ECD different from that seen by HERCEPTIN® was used as a coat to capture ECD including ECD molecules that carry HERCEPTIN® antibody. The HERCEPTIN® thus captured was measured by a suitable detection antibody to form an assay for HERCEPTIN® bound to ECD. To simultaneously capture free HERCEPTIN®, ELISA plates were dual coated with two MAbs: 7C2 to capture ECD-bound HERCEPTIN®, and AMER5 to capture free HERCEPTIN®. Table 2 shows the effect of varying the concentrations of the two MAbs as coat reagents. HERCEPTIN® was spiked into neat human serum at 3.13 µg/ml with or without ECD at 20 µg/ml, diluted 1:100 in Assay Diluent (PBS pH 7.2, 0.05% BSA [bovine serum albumin], 0.05% Polysorbate 20, 0.01% Thimerosal), and assayed using HRP-Goat anti-human IgG Fc at 1:1000 dilution and OPD (o-phenylenediamine, 5 mg in 12.5 ml 4 mM $H_2O_2$ in PBS) as substrate for the enzyme reaction. The reaction was stopped with 4.5 N sulfuric acid and read at 490 nm for absorbance and 405 mn for reference absorbance.

TABLE 2

| Coat AMER5 µg/ml | Coat 7C2 µg/ml | OD of blank, 1% serum | OD of HERCEPTIN® 31 ng/ml 1% serum | OD of HERCEPTIN® 31 ng/ml 1% serum + ECD 200 ng/ml | OD with ECD as % of OD without ECD (blank subtracted) |
|---|---|---|---|---|---|
| 40 | 40 | 0.759 | 1.842 | 1.834 | 99 |
| 20 | 20 | 0.749 | 1.865 | 1.811 | 95 |
| 10 | 10 | 0.642 | 1.814 | 1.766 | 96 |
| 5 | 5 | 0.641 | 1.822 | 1.576 | 79 |
| 2.5 | 2.5 | 0.536 | 1.775 | 1.322 | 63 |
| 1.25 | 1.25 | 0.355 | 1.508 | 0.858 | 44 |
| 0.63 | 0.63 | 0.194 | 0.633 | 0.325 | 30 |
| 10 | 5 | 0.738 | 1.857 | 1.661 | 83 |
| 10 | 2.5 | 0.698 | 1.852 | 1.623 | 80 |
| 10 | 1.25 | 0.658 | 1.814 | 1.506 | 73 |
| 5 | 10 | 0.767 | 1.817 | 1.643 | 83 |
| 2.5 | 10 | 0.754 | 1.644 | 1.632 | 99 |
| 1.25 | 10 | 0.762 | 1.389 | 1.632 | 139 |

As shown in Table 2, the absorbance response was very similar with and without ECD at high and equal concentrations of AMER5 and 7C2 (10, 20 or 40 µg/ml of each). However, ECD inhibited the response when lower concentrations of each coat reagent was used (5, 2.5, 1.25 or 0.63 µg/ml of each), or when 7C2 was used at low concentrations (10 µg/ml AMER5 and 5, 2.5 or 1.25 µg/ml of 7C2). The preferred coat concentrations are 10 µg/ml each of AMER5 and 7C2.

The use of different assay diluents at each step of the procedure, to reduce background and maintain specificity of signals, was also investigated. Blocking and sample incubation was tested in Assay Diluent pH 7.2 (as above), and in Assay Diluent with pH adjusted to 8.0 and to 6.5, and in LA buffer (PBS pH 6.3, 0.5% BSA, 0.05% Tween 20, 5 mM EDTA [(ethylenedinitrilo)tetraacetic acid], plus 0.35 M NaCl), and in MB Buffer (PBS, pH 6.3, 0.5% BSA, 0.05% Tween 20, 5 mM EDTA[(ethylenedinitrilo) tetraacetic acid], 0.25% CHAPS [3-(3-cholamidopropyl) dimethylammoniol)-1-propane-sulfonate], 0.2% BGG (bovine gamma globulin) and 0.35 M NaCl). A preservative was added to each buffer, either 0.01% Thimerosal or 0.05% Proclin 300 (Catalog #5W91 from Supelco). The Assay Diluent pH 7.2, LA buffer and MB buffer were also tested at the conjugate incubation step with various combinations of blocking and sample incubation buffers.

The preferred format is to dual-coat each coat MAb at 10 µg/ml in 0.05 M carbonate buffer, pH 9.5, perform blocking and sample incubation in MB buffer, and peroxidase-conjugated goat anti-human IgG Fc in Assay Diluent, pH 7.2. The calibrators for the standard curve are prepared in MB buffer. Samples are accurately read in serum after a minimum 1:100 dilution in buffer. The resulting assay has a range of 1.56 ng/ml to 100 ng/ml in buffer with a reporting range of 4 ng/ml to 50 ng/ml in 1% human serum.

TABLE 3

| HERCEPTIN® µg/ml serum | ECD µg/ml serum | % Recovery | % CV |
|---|---|---|---|
| 50 | 4 | 104 | 0.4 |
| 25 | 4 | 97 | 7.1 |
| 12.5 | 4 | 100 | 8.5 |
| 6.25 | 4 | 100 | 0.7 |
| 3.13 | 4 | 97 | 5.0 |
| 1.56 | 4 | 88 | 1.1 |

The recovery of HERCEPTIN® in the presence of ECD, read off the standard curve in buffer, was compared to recovery in the absence of ECD. Mean of three experiments, samples assayed in duplicate in each experiment. Results presented in Table 3 show that the assay recovers serum levels of HERCEPTIN® quantitatively in the presence of up to 4 µg ECD/ml serum, the approximate highest levels of ECD expected in clinical trials.

In the next experiment, HERCEPTIN® was spiked into normal human serum at 0.2 to 50 µg/ml. Samples were diluted a minimum of 1:100 and further 1:2 dilutions were made as necessary to cover the working range of the assay. Dilutions were assayed in duplicate and all values within the reporting range were averaged. Each starting concentration was assayed in at least 11 different plates on a number of different days. Table 4 shows that the mass accuracy is within 5% of expected values from 0.4 to 50 µg HERCEPTIN®/ml serum, the highest concentration tested.

TABLE 4

| µg HERCEPTIN®/ml serum | % Recovery | % CV |
|---|---|---|
| 50 | 101 | 2.3 |
| 25 | 97 | 6.5 |
| 12.5 | 104 | 6.3 |
| 6.25 | 102 | 4.7 |
| 3.13 | 99 | 5.9 |
| 2.0 | 98 | 3.1 |
| 1.0 | 96 | 7.4 |
| 0.8 | 99 | 5.2 |
| 0.6 | 97 | 5.9 |
| 0.4 | 96 | 9.1 |
| 0.2 | 86 | 18.8 |

Figure 3:
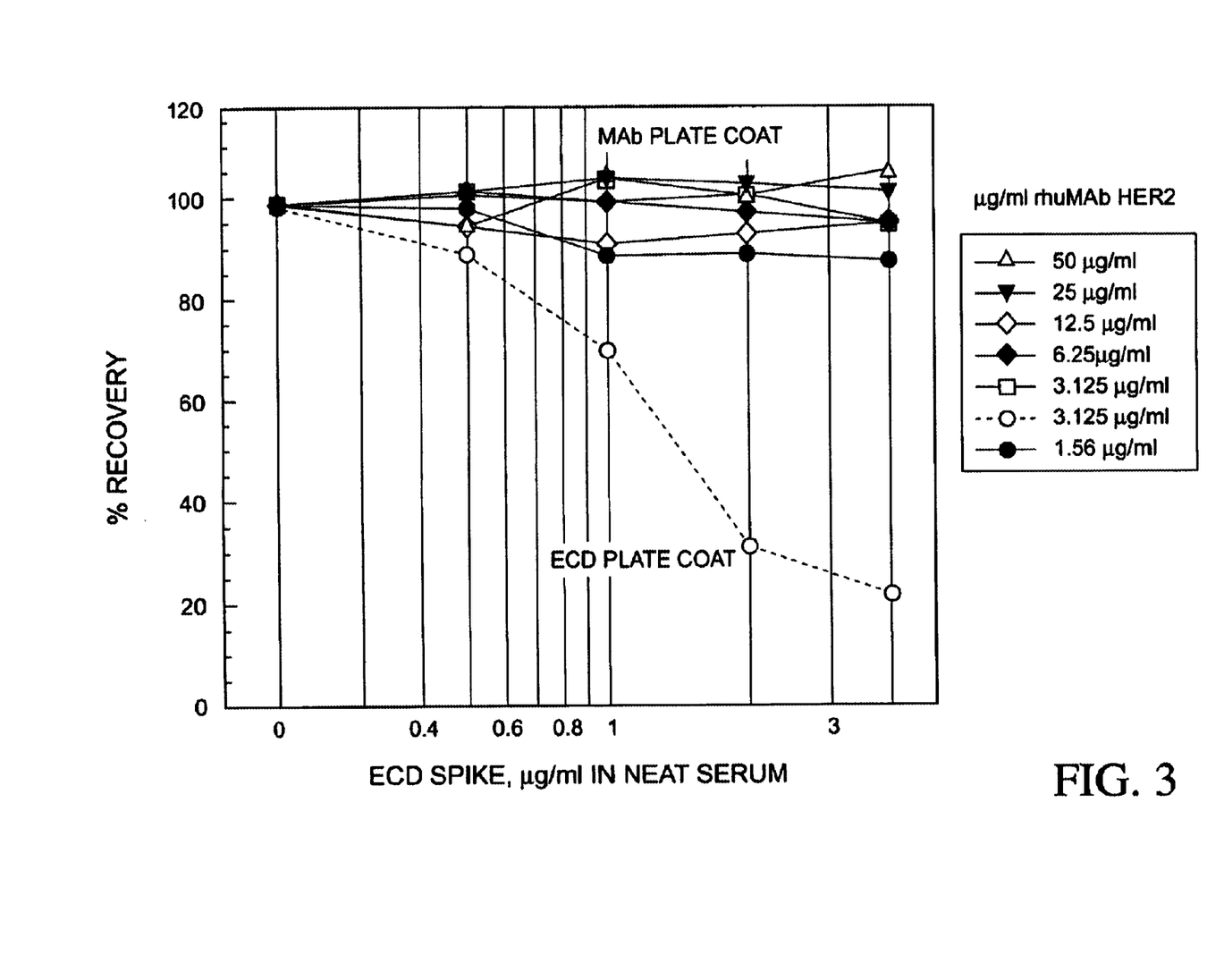
FIG. 3 shows recovery of free and ECD-complexed anti-HER2 in a dual-coat ELISA. Monoclonal antibodies against HERCEPTIN® (AMER5) and ECD (7C2) were used at various ratios in order to optimize the dual coat strategy.

The resulting assay quantitatively measures HERCEPTIN® in the presence of three-fold weight excess of ECD. A representative example is shown in FIG. 3. MAb 7C2 (anti-ECD) and MAb AMER5 (anti-anti-HER2) were both coated on ELISA wells at 10 µg/ml. Plates were blocked, samples added and detected as in FIG. 2. Results show that for a 2 h sample incubation, anti-HER2 was quantitatively recovered in the presence of ECD at concentrations up to 4 µg/ml serum in the dual-coat format, but not in the original format with the ECD coat capture (ECD Plate Coat).

All references cited throughout the specification, and all references cited therein are hereby expressly incorporated by reference.

It is understood that the application of the teachings of the present invention to a specific problem or situation will be within the capabilities of one having ordinary skills in the art in light of the teachings contained herein. Examples of the methods and products of the present invention should not be construed to limit the invention.

Deposit of Materials

The following hybridoma cell line has been dposited with the American Type Culture Collection, 10801 University Boulevard, Manassas, Va. 20110-2209 USA (ATCC):

Antibody Designation ATCC No. Deposit Date
7C2 ATCC HB-1215 Oct. 17, 1996

This deposit was made under the provisions of the Budapest Treaty on the International Recognition of the Deposit of Microorganisms for thr Purpose of Patent Procedure and the Regulations thereunder (Budapest Treaty). This assures maintenance of a viable culture of the deposit for 30 years from the date of deposit. The deposits will ipe made available by ATCC under the terms of the Budapest Treaty, and subject o an agreewent between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patent and Trademarks to be entitled thereto according to 35 USC § 122 and the Commissioner's rules pursuant thereto (including 37 CFR § 1.14 with particular reference to 886 OG 638).

What is claimed is:

1. A method for determining the total amount of an anti-HER2 antibody in a fluid sample in the presence of HER2 extracellular domain (ECD), comprising:
   (a) providing a solid surface dual-coated with first antibody recognizing said anti-HER2 antibody in a free form and a second antibody recognizing said HER2 ECD when bound to said anti-HER2 antibody;
   (b) contacting said dual-coated surface with said fluid sample, whereby said first antibody binds said free anti-HER2 antibody and said second antibody binds said HER2 ECD bound to said anti-HER2 antibody; and
   (c) determining the total amount of said free anti-HER2 antibody and said anti-HER2 antibody bound to said HER2 ECD by contacting the product of step (b) with a detectably labeled secondary antibody recognizing said anti-HER2 antibody, wherein said detectably labeled secondary antibody recognizes an epitope which is different from the epitope recognized by said first antibody and is also different from the epitope recognized by said HER2 ECD, and
   wherein the total amount of said free anti-HER2 antibody and said anti-HER2 antibody bound to said HER2 ECD is compared with a standard curve generated by using various concentrations of said purified anti-HER2 antibody in place of said fluid sample in step (b).

2. The method of claim 1, wherein said first and second antibodies are polyclonal antibodies.

3. The method of claim 1, wherein said first and second antibodies are monoclonal antibodies.

4. The method of claim 1, wherein said detectable label is an enzyme conjugated to said secondary antibody.

5. The method of claim 4, wherein said enzyme is peroxidase.

6. The method of claim 5, wherein said peroxidase is horseradish peroxidase.

7. The method of claim 4, wherein said enzyme is alkaline phosphatase.

8. The method of claim 4, wherein said enzyme is detected using a substrate for said enzyme.

9. The method of claim 8, wherein said substrate is ortho-phenylene diamine (OPD) for the detection of said peroxidase.

10. The method of claim 1, wherein sail solid surface is in a configuration of a test tube, a well, bead, a rod, or a trip.

11. The method of claim 10, wherein said configured solid surface is glass, plastic, or paper.

12. The method of claim 11, wherein said plastic is polystyrene or polyacrylate.

13. The method of claim 1, wherein said fluid sample comprises a biological fluid.

14. The method of claim 13, wherein sad biological fluid comprises serum or plasma.

15. The method of claim 1, wherein said anti-HER2 antibody is a murine monoclonal antibody.

16. The method of claim 15, wherein said murine anti-HER2 monoclonal antibody is 4D5.

17. The method of claim 16, wherein said anti-HER2 murine monoclonal antibody is a humanized version of recombinant 4D5 antibody.

18. The method of claim 17, wherein said humanized version of recombinant 4D5 anti-HER2 antibody is huMAb4D5-8 (rhuMAb HER2).

19. The method of claim 18, wherein said first antibody recognizes huMAb4D5-8 (rhuMAb HER2) and does not significantly cross-react with hum IgG, and said second antibody against HER2 ECD is a polyclonal or a monoclonal antibody.

20. The method of claim 19, wherein said first antibody recognizing huMAb4D5-8 (rhuMAb HER2 is a monoclonal antibody or a fragment derived th from, and said monoclonal antibody against HER2 ECD is 7C2 (ATCChB-12215).

21. The method according to any one of the claims 15-18, wherein said fluid sample is serum or plasma derived from a cancer patient undergoing anti-HER2 therapy.

22. The method of claim 21, wherein said cancer is breast cancer overexpressing HER2.

* * * * *

UNITED STATES PATENT AND TRADEMARK OFFICE
CERTIFICATE OF CORRECTION

PATENT NO. : 6,984,494 B2
APPLICATION NO. : 09/921161
DATED : January 10, 2006
INVENTOR(S) : Peter Ralph It is certified that error appears in the above-identified patent and that said Letters Patent is hereby corrected as shown below:

Claim 10 (column 24, line 6&7) "The method of claim 1, wherein sail solid surface is in a configuration of a test tube, a well, bead, a rot, or a trip" should read --The method of claim 1, wherein said solid surface is in a configuration of a test tube, a well, bead, a rot, or a strip--

Claim 14 (column 24, line 14) "The method of claim 13, wherein sad biological fluid comprises serum or plasma" should read --The method of claim 13, wherein said biological fluid comprises serum or plasma--

Claim 19 (column 24, line 26) "The method of claim 18, wherein said first antibody recognizes huMAb4D5-8 (rhuMAb HER2) and does not significantly cross-react with hum IgG , and said second antibody against HER2 ECD is a polyclonal or a monoclonal antibody" should read --The method of claim 19, wherein said first antibody recognizes huMAb4D5-8 (rhuMAb HER2) and does not significantly cross-react with human IgG , and said second antibody against HER2 ECD is a polyclonal or a monoclonal antibody--

Claim 20 (column 24, line 32/33) "The method of claim 19, wherein said first antibody recognizing huMAb4D5-8 (rhuMAb HER2 is a monoclonal antibody or a fragment derived th from and said monoclonal antibody against HER2 ECD is 7C2 (ATCChB-12215)". should be --The method of claim 19, wherein said first antibody recognizing huMAb4D5-8 (rhuMAb HER2) is a monoclonal antibody or a fragment derived therefrom and said monoclonal antibody against HER2 ECD is 7C2 (ATCC HB-12215)--.

Signed and Sealed this

Sixth Day of March, 2007

JON W. DUDAS
*Director of the United States Patent and Trademark Office*